United States Patent
Kenley et al.

(10) Patent No.: US 9,345,826 B2
(45) Date of Patent: May 24, 2016

(54) RECIRCULATING FLUID FILTRATION SYSTEM

(75) Inventors: Rodney S. Kenley, Libertyville, IL (US); Ryan K. LaRocque, Pepperell, MA (US); Andrew A. Schnellinger, Merrimack, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 13/619,010

(22) Filed: Sep. 14, 2012

(65) Prior Publication Data

US 2013/0248450 A1  Sep. 26, 2013

Related U.S. Application Data

(60) Provisional application No. 61/535,135, filed on Sep. 15, 2011.

(51) Int. Cl.
*B01D 49/00* (2006.01)
*C02F 3/12* (2006.01)
*A61M 1/16* (2006.01)
*A61M 1/34* (2006.01)
(Continued)

(52) U.S. Cl.
CPC ............... *A61M 1/16* (2013.01); *A61M 1/3472* (2013.01); *A61M 1/3482* (2014.02); *A61M 1/3486* (2014.02); *A61M 1/3601* (2014.02); *A61M 1/3624* (2013.01); *A61M 1/3679* (2013.01); *B01D 24/48* (2013.01); *B01D 37/04* (2013.01)

(58) Field of Classification Search
CPC ... A61M 1/16; A61M 1/3486; A61M 1/3472; A61M 1/3482
See application file for complete search history.

(56) References Cited

U.S. PATENT DOCUMENTS 3,552,574 A  1/1971  Lowe et al.
3,627,131 A * 12/1971 Goodman et al. ............ 210/741
(Continued)

FOREIGN PATENT DOCUMENTS

WO  WO 02/055182 A1  7/2002

OTHER PUBLICATIONS

Ahmad, *Essentials of Water Treatment in Hemodialysis*, Dialysis/Apheresis, University of Washington, Scribner Kidney Center, Northwest Kidney Center, Seattle, Washington, U.S.A., Hemodialysis International 2005; 9: pp. 127-134.
(Continued)

*Primary Examiner* — Nam Nguyen
*Assistant Examiner* — Richard Gurtowski
(74) *Attorney, Agent, or Firm* — Marc J. Gorayeb

(57) ABSTRACT

A fluid filtration system comprising a cross-flow filter is arranged to permit a first pump to recirculate part of the retentate of the filter to the inlet of the cross-flow filter and a second pump to return part of the permeate to the inlet of the cross-flow filter. A third pump is configured supply source fluid to the inlet of the filter. The flow path between the second pump and the cross-flow filter inlet may include an adsorption filter that may selectively remove contaminants, toxins, or pathogens in the permeate. A controller may control the first, second and third pumps to provide predetermined flow ratios among the fluid flow paths of the system in order to achieve a desired filtration level. This system may be applicable to the removal of harmful substances from blood, by first separating the plasma from the blood and then removing harmful substances from the plasma.

16 Claims, 4 Drawing Sheets

(51) Int. Cl.
  *A61M 1/36* (2006.01)
  *B01D 37/04* (2006.01)
  *B01D 24/48* (2006.01)

(56) References Cited

U.S. PATENT DOCUMENTS

| | | | | |
|---|---|---|---|---|
| 3,637,467 | A | * | 1/1972 | Spatz .......................... 205/100 |
| 3,756,408 | A | | 9/1973 | Spatz et al. |
| 3,923,654 | A | * | 12/1975 | O'Hern et al. ........... 210/500.25 |
| 4,243,883 | A | * | 1/1981 | Schwarzmann .............. 250/343 |
| 4,735,716 | A | * | 4/1988 | Petrucci et al. ............... 210/232 |
| 4,959,237 | A | | 9/1990 | Walker |
| 5,120,900 | A | | 6/1992 | Chen et al. |
| 5,194,157 | A | * | 3/1993 | Ghezzi et al. ................ 210/646 |
| 5,234,606 | A | | 8/1993 | Kazama et al. |
| 5,651,894 | A | | 7/1997 | Boyce et al. |
| 5,919,357 | A | * | 7/1999 | Wilkins et al. ................ 210/120 |
| 5,935,441 | A | * | 8/1999 | O'Neill et al. ................ 210/638 |
| 6,228,255 | B1 | | 5/2001 | Peterson et al. |
| 6,328,896 | B1 | | 12/2001 | Atnoor et al. |
| 7,122,149 | B2 | | 10/2006 | Li et al. |
| 7,407,585 | B2 | | 8/2008 | Gaignet |
| 2008/0023410 | A1 | | 1/2008 | Efraty |

OTHER PUBLICATIONS

Brendolam et al., *Coupled Plasma Filtration Adsorption: Rationale, Technical Development and Early Clinical Experience*, Ronco C, Bellomo R, Brendolan A (eds): Sepsis, Kidney and Multiple Organ Dysfunction. Contrib Nephrol. Basel, Karger, 2004, vol. 144, pp. 376-386.

Brendolan et al., *Double Pass Dialysis: A New Method of Renal Replacement in Patients with Malfunctioning Vascular Access*, The International Journal of Artificial Organs/vol. 17/No. 7, 1994, pp. 379-384.

Williams et al., *Evaluation of a Kinetic Model for Predilution Plasmapheresis*, Therapeutic Apheresis: A Critical Look, Edited by Y. Nose PS Malchesky and JW Smith; ISAO Press, Cleveland 1984, pp. 241-246.

International Search Report and Written Opinion dated May 8, 2013, received in International patent application PCT/US2012/055524, 15 pgs.

\* cited by examiner

RECIRCULATING FLUID FILTRATION SYSTEM

CROSS-REFERENCE TO RELATED APPLICATIONS

This application claims the benefit of U.S. Provisional Patent Application Ser. No. 61/535,135, filed Sep. 15, 2011, and entitled Optimized Flow Loop for Fluid Filtration, which is hereby incorporated by reference herein in its entirety.

TECHNICAL FIELD

The present invention relates to fluid filtration systems and methods.

BACKGROUND

In chemical engineering, biochemical engineering and protein purification, cross-flow filtration (also known as tangential flow filtration) is a type of filtration where the majority of the feed flow travels tangentially across the surface of the filter, rather than through the filter. The permeate passes through the filter membrane or filter media, while the retentate exits the filter body carrying the particles too large to pass through the filter element. A range of different types of membranes are available that can be characterized by the size of the particles and solutes that do not pass through the membrane. For example, in biological applications, plasma filters have microfiltration membranes that retain cells and other particles larger than about 1 μm in the retentate, while allowing smaller particles (e.g., proteins) to pass through with the permeate. Also, ultrafilters—filters used to concentrate proteins—retain particles larger than 10 kiloDalton. Nanofiltration generally involves filtering with a pore size of about 0.001 micron, and can remove most organic molecules, viruses, salts and divalent ions. Reverse osmosis—the most restrictive filtration with filters having a pore size of about 0.0001 micron retains all particles and solutes including monovalent ions and most minerals. The principal advantage of cross-flow filtration is that the filtered particles and solute are substantially washed away from the filter surface during the filtration process, increasing the length of time that a filter unit can be operational.

Flow systems typically control certain conditions such as, for example, pressure and flow rate, to achieve a preferred performance. The blood pumping system of an extracorporeal blood purification system, for example, is selected or configured so that the range of pressure and flow rate may be preferentially optimized for the characteristics of a given patient access. However such systems may have particular components (such as a plasma filter in the case of an extracorporeal blood treatment system) whose optimal operating conditions differ from the preferred operating conditions of the system as a whole. In the following description, the term solute is intended to broadly include molecules, compounds or other substances dissolved in the fluid. Examples of solutes include but are not limited to salts or sugars. In the following description, the term particle is intended to broadly include compounds, polymers, solid structures, biological cells, parts of cells, macro molecules, protein structures, etc. that are carried by the fluid in a mixture or in suspension. Examples of particles include but are not limited to whole blood cells, bacteria, viruses and proteins.

SUMMARY OF INVENTION

A fluid purification system comprises a cross-flow filter, a fluid conduit to re-circulate reject fluid or retentate from the filter, a $1^{st}$ pump to drive the recirculation, a $2^{nd}$ pump to supply fresh fluid to system and an exiting fluid conduit comprising a flow resistor to allow some of the retentate to exit the system. The cross-flow filter includes an inlet port, a $1^{st}$ outlet port where retentate exits the filter, and a $2^{nd}$ outlet port through which the filtered liquid permeate exits. Liquid from the $1^{st}$ outlet port flows to the inlet port via the recirculation loop. Flow through the recirculation loop and filter is driven by the $1^{st}$ pump. Fresh fluid is supplied to the recirculation loop by a $2^{nd}$ pump. A portion of the retentate exits the recirculation loop via a fluid conduit that includes a flow resistor. The $2^{nd}$ pump supplies enough fluid flow to achieve a desired pressure in the filter given the flow resistances of the filter membrane and flow resistor.

In an embodiment, a two-tiered pumping system may be used, comprising two or more pumps. A feed booster pump supplies fluid from a fluid source and delivers it to the feed fluid recirculation circuit. The pump flow rate can be relatively small—enough to replace the filtered fluid output of the cross-flow filter and any additional fluid discharged from the recirculation circuit. The feed booster pump in combination with a pressure relief device maintains the desired pressure in the recirculation circuit for optimal operation of the filter. In an embodiment, with a filter suitable for use in filtering plasma, the feed booster pump and a flow restriction coil are configured to maintain a recirculation circuit pressure of between approximately 16 kPa and 26 kPa (2.3 psig and 3.8 psig) and an average inlet flow rate of approximately 100 ml/min. Alternatively, when the system is configured with an ultrafilter, the feed booster pump and a flow restriction coil are configured to maintain a recirculation circuit pressure of between approximately 100 kPa and 410 kPa (15 and 60 psig) and an average inlet flow rate of approximately 200 ml/min.

A feed fluid recirculation pump can be included to circulate fluid through the feed fluid recirculation circuit that comprises a fluid conduit fluidly connecting the retentate outlet of a filter in the circuit with the inlet of the recirculation pump. Preferably, the flow rate generated by the feed fluid recirculation pump is sufficiently high to optimize the filtering characteristics of the filter and minimize the frequency of cleaning operations. A high flow rate may increase the flux of fluid through the cross-flow filter membrane. A high flow rate may also help to prevent build-up of mineral scale deposits and biofilm, which reduce the cross-flow filter's effectiveness and lifespan. A high flow rate may also reduce damage to cells by concentrating them near the center of the fluid flow path and away from the walls of the conduit through which the fluid is flowing. In an embodiment configured with a plasma filter, the flow rate generated by the feed fluid recirculation pump can be in the range of 100-250 ml/min during fluid filtering and production operations. Alternatively, in a configuration with an ultrafilter, the feed fluid recirculation pump can provide about 300-700 ml/min during fluid filtering. The flow rate of the recirculation pump can be optionally lower during periods when demand for filtered fluid or permeate is reduced or nonexistent.

Although the feed fluid recirculation pump may operate in a recirculation circuit that is maintained at a relatively high average pressure (e.g., 400 kPa), the feed fluid recirculation pump need only generate a differential pressure sufficient to overcome the pressure drop across the feed-through side of the filter. In an embodiment wherein the filter comprises an ultrafiltration membrane, the pressure drop through the feed side of the filter typically can be less than 172 kPa (25 psi). Thus, the net power consumption of the feed pump and feed fluid recirculation pump together (feed pump—high pressure differential/low flow, feed fluid recirculation pump—low pressure differential/high flow) can be significantly less than the power consumption of a single-pump system that needs to generate both the high pressure and the high flow rate required for optimal operation of a membrane filter with very small pores such as an ultra filter.

DETAILED DESCRIPTION OF PREFERRED EMBODIMENTS

The term "downstream" as used herein indicates a position in the flow path, with respect to a current position or point of discussion, which will be reached in time with the normal movement of fluid through the system. Arrowheads along the flow path in the figures indicate the normal direction of fluid flow. The term "upstream" may be used to indicate a position in a direction that opposes normal fluid flow, i.e., opposes the direction of the arrowheads.

Figure 1:
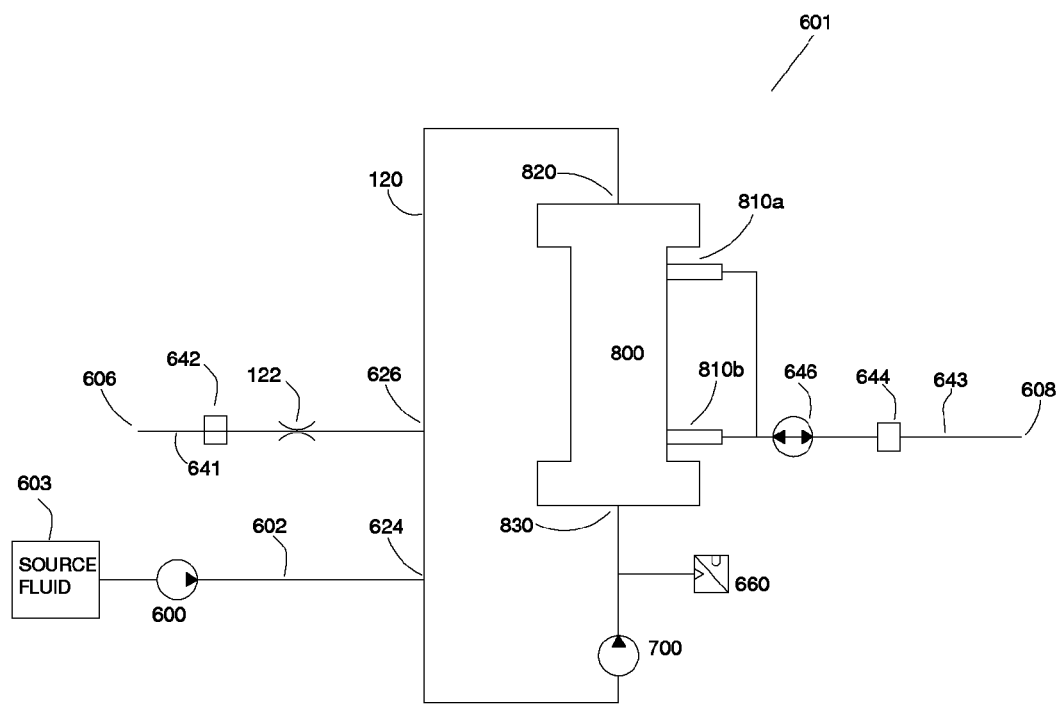
FIG. 1 is a schematic representation of a cross-flow filter with return loop.

FIG. 1 shows basic elements of cross-flow filter system 601 that comprises a cross-flow filter 800, a return loop 120, a supply/booster pump 600 and recirculation pump 700. The cross-flow filter system 601 filters the feed fluid from the source 603, delivers the filtered fluid or permeate to port 608, while delivering concentrated feed or retentate to port 606. In other embodiments the cross-flow filter system 601 may be part of a larger system that may have preferred operating parameters including but not limited to supply pressure, supply flow rates, or product flow rates. The product may be the retentate at port 606 or the permeate at port 608 or fluid from both ports may be used by the larger system.

A feed recirculation loop 120 may be used to maintain a high rate of fluid flow on the feed side of the membrane of the cross-flow filter 800, reducing the amount of feed fluid that otherwise would be discarded to drain. The entire recirculation loop 120 may be pressurized sufficiently to permit filtration of fluid in the filter 800 at a rate required by a larger system receiving the fluid product of cross-flow filter system 601. In an embodiment in which the filter 800 is a plasma filter, the flow rate generated by the feed fluid recirculation pump 700 can be in the range of 100-250 ml/min during fluid filtering and production operations. Preferably, a feed booster pump 600 can boost the feed pressure and maintain a hydrostatic pressure of between approximately 16 kPa and 26 kPa (2.3 psig and 3.8 psig) in the feed recirculation loop 120. In embodiments in which the filter 800 is an ultrafilter, the flow rate generated by the feed fluid recirculation pump 700 may be in the range of 300-700 ml/min during fluid filtering and production operations. In an arrangement with an ultrafilter, the booster pump 600 may boost the feed pressure and maintain a hydrostatic pressure of between approximately 100 kPa and 410 kPa (15 and 60 psig) in the feed recirculation loop 120.

The pressurization of the recirculation loop can be accomplished, for example, by a feed booster pump 600 combined with a flow restrictor 122 and filter 800. The booster pump 600 can be provided with source fluid 603 at a rate sufficient to match the amount of permeate fluid at outlet 810a and 810b of filter 800, plus any amount of retentate flow through flow restrictor 122 and out of the filter system via conduit 641.

In order to maintain the desired hydrostatic pressure developed by the booster pump 600 in the recirculation loop 120, the desired permeate flow from the filter 800, and the desired fresh feed replenishment via pump 600, a flow restrictor 122 may be introduced in the flow path between recirculation loop 120 and outlet port 606. This may simply comprise a small orifice in a conduit connecting recirculation loop 120 and exit port 606, a needle valve or other variable orifice valve, or a restriction coil, among other possibilities. An advantage of a restriction coil may include the possibility of reducing turbulent flow and cavitation across the restriction, thereby reducing noise and component wear or erosion. A further advantage of the restriction coil is that it may provide laminar flow restriction that effectively limits flow predictably over a wide range of pressures and flow rates. In addition, it may be possible to optimize the flow resistance of the restriction coil in the field by merely trimming the length of the coil. It may be advantageous to incorporate both a fixed flow restrictor such as a restriction coil, as well as a variable valve in order to allow a controller to control the net resistance to flow from recirculation loop 120 to exit port 606. Valve 642, for example, may incorporate a variable orifice.

It may be advantageous to limit the maximum pressure in the recirculation loop 120 and the filter to prevent damage to the filter and tubing. The maximum pressure in the recirculation loop 120 may be limited, for example, by a pressure limiting valve (not shown) that opens when the upstream pressure exceeds a pre-determined value. The pressure limiting valve may be a back-pressure regulator that allows a variable amount of flow in order to limit the upstream pressure below a pre-determined value. Alternatively the pressure limiting valve may be a relief valve that provides gradual pressure relief. Or it may be a pop-safety valve that opens fully at a pre-determined pressure. The back pressure limiting valve may be built into or associated with the booster pump 600. Alternatively the back pressure limiting valve may be installed in place of the flow restrictor 122 or may be plumbed in parallel to the flow restrictor 122. In an embodiment comprising a plasma filter in which there is little pressure restriction on the permeate flow, the recirculation pressure may be limited to approximately 25 kPa (3.6 psig) in order to protect the membrane. In an embodiment comprising an ultrafilter the recirculation pressure may be limited to approximately 410 kPa (60 psig).

Feed booster pump 600 is preferably configured to boost pressure in the recirculation loop 120, which can be achieved through the use of a positive displacement pump. Generally, this type of pump can produce a desired flow rate at a wide range of output pressures. A check valve (not shown) optionally may be positioned near the inlet of pump 600 to prevent feed fluid at high pressures from bleeding back toward the source 603. The flow rate of the booster pump 600 may be selected to produce the desired flow rate of permeate fluid from filter 800, plus the flow rate of retentate via conduit 641. Knowing the desired flow rates of permeate and retentate and the desired pressure range in the recirculation loop 120, the characteristics of flow restrictor 122 may be determined either analytically or empirically.

Figure 2:
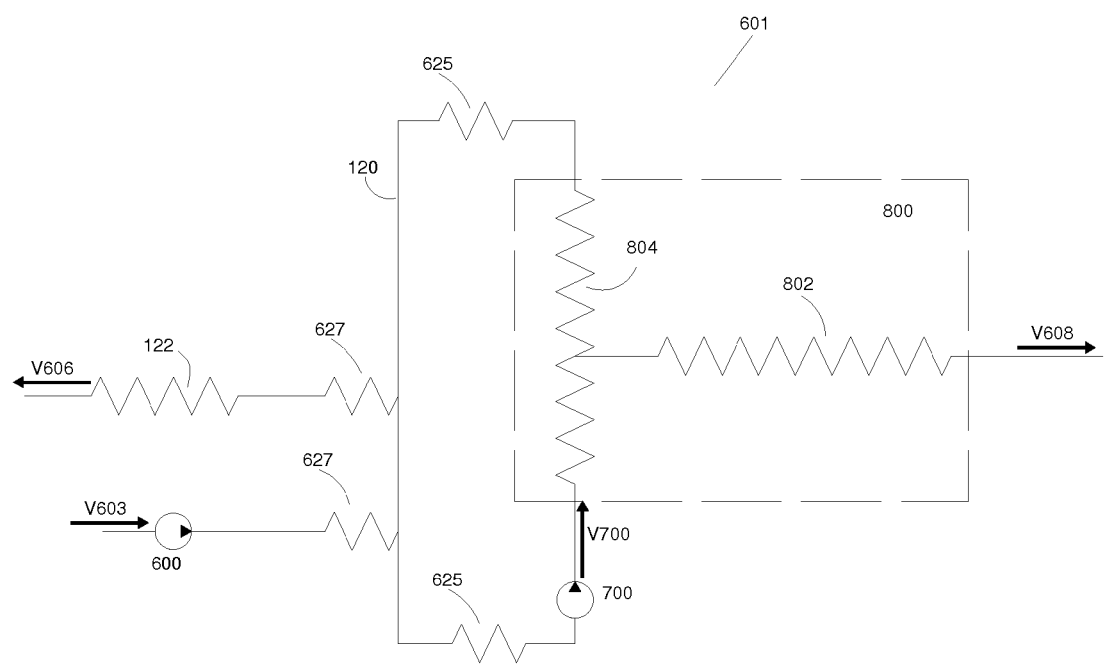
FIG. 2 is a conceptual model of a fluid flow network of an exemplary fluid filtration system.

One example of a method to analytically determine the desired characteristics of the flow restrictor 122 based on the recirculation loop pressure may be illustrated by the flow schematic shown in FIG. 2. The two pumps 600, 700 may be idealized to be constant flow sources in the case of displacement pumps or to be constant pressure sources in the case of centrifugal pumps. Alternatively the pump models may be derived from empirical flow vs. pressure curves. In another embodiment, one or both pump models may be treated as a pneumatically driven diaphragm pump that produces constant flow up to a given maximum pressure at which point the flow goes to zero. The schematic in FIG. 2 includes flow resistances of the flow resistor 122, flow through the filter 804, across the membrane 802, tee fittings 627 and flow resistance of the recirculation loop 625. The flow restriction of the flow resistor $R_{122}$ can be estimated by neglecting the minor resistances $R_{625}$, $R_{627}$ and using the filter inlet pressure P, the product flow rate $V_{608}$, the flow ratio of product over supply ($Y=V_{608}/V_{603}$), the flow ratio of recirculation over supply ($Z=V_{700}/V_{603}$) and the flow resistance through the filter on the feed side $R_{804}$ as:

$$R_{120} = \frac{P_{804}}{V_{603} \cdot Y} \cdot \left(\frac{1}{Y-1}\right) - \frac{R_{804}}{2} \cdot Z \cdot \left(\frac{1}{Y-1}\right).$$

In an embodiment, the flow resistor 122 may be a restriction coil 122. The length and the diameter of the tubing may be selected to achieve the desired flow resistance. The diameter may be selected to assure laminar flow in a wide range of flow rates. The appropriate balance between tubing length and diameter will depend on a number of characteristics, including the amount of space the restriction coil occupies, the cost of materials, and the amount of noise it generates, among other factors. The diameter may be selected to assure laminar flow at most of the desired flow rates. The flow resistance may be adjusted in the field, for example, by trimming the length of the restriction coil 122.

If un-replenished feed were to circulate through loop 120, its solute or particulate concentration would progressively increase as the filter 800 continued to produce purified permeate. Eventually, the solute or particulate concentration of the recirculating feed could increase to the point of impairing the performance of filter 800, resulting in a reduction in permeate output or quality, and/or premature fouling of the filter membrane. This may also eventually occur if feed replenishment is limited to the amount of permeate generated by the filter 800. The level of solute or particulate concentration in the recirculating loop may be stabilized by constantly replacing a portion of the retentate (or reject liquid) with fresh fluid via the supply pump 600. The steady state level of solute or particulate concentration in the recirculating loop ($X_{606}$) may be estimated, for example, from the feed concentration ($X_{603}$) and the flow ratio of product over supply ($Y=V_{608}/V_{603}$):

$X_{606}=X_{603}/(1-Y)$

The constant replenishment of the recirculating loop 120 by fresh feed fluid may be achieved by having the booster pump 600 supply feed fluid at a rate above the flow rate of permeate ($V_{608}$), and allowing a fraction of the retentate or reject liquid to flow through the flow restrictor 122 to the drain line 641. The concentration of the retentate in the recirculating loop 120 may be controlled by selecting a flow restrictor 122 with the appropriate resistance, or by otherwise adjusting the resistance of flow restrictor 122.

Alternatively, the desired characteristics of the flow restrictor 122 may be calculated based on concentrations of a particular solute or particle and the pressure drop characteristics of the cross-flow filter 800. The desired flow resistance of the flow restrictor can be estimated in the following equation if one assumes a negligible concentration of the solute or particle of interest in the permeate. The flow resistance of flow restrictor 122 may be derived from the ratio of the feed concentration over the desired retentate concentration of a given solute or particulate ($XR=X_{603}/X_{606}$), the ratio of recirculation flow over supply flow ($Z=V_{700}/V_{603}$) and the flow resistances of the filter R802, R804.

$$R_{120} = R_{802} \cdot \left(\frac{1-XR}{XR}\right) - \frac{R_{804}}{2} \cdot \left(\frac{Z}{XR}\right)$$

If the feed pump 600 is a positive displacement pump operating at a fixed rate, then increasing the resistance offered by flow restrictor 122 will reduce the retentate fraction and increase the production rate of permeate. However, if a lower output of permeate is desired, or if the solute or particulate concentration of the feed source is less than expected, it may be advantageous to increase the resistance to the flow of fluid from loop 120 to drain line 641, while concurrently reducing the pumping rate of booster pump 600.

A controllable variable restriction feature can be incorporated, for example, into valve 642. The solute or particulate content of the recirculating feed fluid may be monitored, for example, by a conductivity sensor (or other types of sensors). A controller can receive the output of the sensor, and implement a pre-determined algorithm to adjust valve 642 to achieve a target net flow resistance between recirculation loop 120 and drain line 641, based on the trend of the recirculating feed fluid conductivity. The controller may vary the flow resistance of the valve 642 to maintain a desired level of solute or particulate concentration in the recirculation loop 120 as measured by the conductivity or other type of sensor.

A fluid recirculation pump 700, positioned within the recirculation loop 120, can boost the fluid flow velocity along the filter membrane sufficiently to improve the filter performance. Typically higher fluid flow rates of along the filter membrane produce higher flux of permeate. Alternatively, higher flow rates in the recirculation loop 120 may allow the booster pump 600 to be operated at a lower pressure for any given flow rate of permeate. In addition, a higher flow rate in the recirculation loop 120 may allow for the use of a filter having a smaller filter area.

Higher fluid flow rates may provide different benefits with different types of cross-flow filter membranes. For example, higher blood flow rates past microfiltration membranes may reduce damage to cells and reduce fouling of the membrane surface. One possible explanation for this effect is that higher laminar flow rates may increase the lifting force on cells, pulling them to the center of the flow path and away from the membrane surface or conduit walls. This transport mechanism is often termed inertial lift. Microfiltration of fluid containing cells or cellular elements may benefit from a recirculation pump that produces a steady flow of fluid. Periodic flow from, for example a single peristaltic pump, could create mixing in the flow paths and breakdown the laminar flow that tends to keep cells away from the filter walls. Rather, an axial pump may allow laminar flow to develop that tends to concentrate the cells away from the membrane surface. Other alternatives for generating steady flow include the use of dual linear peristaltic pumps, dual diaphragm pumps, vane pumps or radial centrifugal pumps. High fluid flow rates may also inhibit adhesion of dissolved or suspended compounds (such as proteins or other macromolecules) to the filter membrane, and thus help to maintain the filtering efficiency of the membrane.

In some cases, turbulent fluid flow across a filter membrane may be preferred. Ultrafiltration and nanofiltration membranes exposed to high fluid flow rates may be used in conjunction with structures (e.g., separators) to increase the mixing of the fluid flowing past the membrane. Increased mixing of the feed fluid in this case may increase the concentration of the permeable elements and compounds at the membrane surface of the filter. The increased flow rate and mixing may also inhibit biofouling or scaling of the membrane surface. Without being bound to a single theory, one possible explanation for reduced fouling at high flow rates is that the fast turbulent flow of fluid over the surface of the membrane creates high shear stress at the membrane surface which agitates or abrades biofilms and other fouling materials that may collect on the membrane surface.

Regardless of the net flow of into and out of the recirculation loop 120, the recirculation pump 700 can boost the flow rate of fluid circulating through the filter 800 via inlet 830 and discharge outlet 820. Thus the booster pump 600, while operating at a relatively high pressure differential, can do so at a relatively low flow rate, while the high-flow recirculation pump 700, while operating at a relatively high flow rate, can do so at a relatively low pressure differential. Separating the pressure-boosting function to operate the filter 800 from the flow-boosting function to maintain a high rate of flow across filter 800 may result in a reduction of net power consumption by the one or more pump motors in the cross-flow filter system 601.

The cross-flow filter 800 may be a commercially available filter module containing a membrane that retains a given type or size of cells, cellular elements, particles or solutes in the retentate, while allowing smaller particles or compounds along with the liquid to past through the membrane to form the permeate. The cross-flow filter membrane may be characterized by the size of particles that are retained in the feed fluid. One example is a microfiltration membrane used to separate intact cells from the rest of the components in the feed fluid. The Prismaflex® System marketed by Gambro Lundia AB, for example, includes a plasma filter (a microfiltration filter) that separates the red blood cells from the plasma. The pores in the microfiltration membrane typically have a size in the range of 0.05 to 1 mm. Ultrafiltration membranes are finer than microfiltration membranes and typically have pore sizes in the range of 10 kiloDaltons up to 500 kiloDaltons. An ultrafiltration membrane may be used to separate proteins from salts, viruses or other proteins. The tightest membranes used in nanofiltration or reverse osmosis separate solutes such as salts and other small molecules with molecular masses less than 1.5 kiloDaltons from water or other solvents.

The filter membrane in the cross-flow filter 800 may be held in any of a number of different modules. Hollow fibers modules are comprised of a bundle of thin fibers in a shell with a manifold at each end to distribute the feed fluid to the center of the many fibers and isolate the feed fluid from the permeate fluid in the shell. The hollow fibers typically have open inner diameters in the range of 0.1 to 2.0 mm. The feed fluid flows through the center of a fiber and the permeate flows through the walls of the fiber to the shell side of the filter module. Hollow fibers are typically used with shear sensitive materials such a blood due to the low shear rates in the fiber centers. Flat plate and spiral wound modules are comprised of layers of membrane with channels connected to the feed manifold, alternating with other channels connected to permeate ports. Separators may be placed in the feed channels to promote turbulent mixing and higher flux of permeable compounds across the membrane. However, separators may increase the flux across the membrane at the expense of higher pumping power and possible damage to intact cells when the feed fluid is a composition of blood elements.

In an embodiment, a pressurized reservoir or vessel (not shown) may be incorporated into the recirculation loop that supplies fluid to the filter. The pressurized reservoir can connected to the loop via a tee fitting or may be in-line with the recirculation flow circuit. The reservoir may be preferentially placed downstream of the filter 800 and upstream of the recirculation pump 700.

A controller (not shown) may monitor the pressure transducer 660 and control the pressure in the recirculation loop by varying the pumps 600, 700 upstream of the filter or the flow control devices downstream of the filter. In one example the controller may vary the speed of the supply pump 600 and/or recirculation pump 700 to maintain the measured pressure at 660 within pre-determined limits. In another example the controller may vary the valves 642, 644 on the retentate and permeate lines 641, 643 to maintain the measured pressure at 660 within pre-determined limits. In another example, the controller may control the pressure is the recirculation loop by controlling the flows through the retentate and permeate lines 641, 643 by pumps such as pump 646 on the permeate line.

Referring to FIG. 1, the pressure in the recirculation loop may be controlled with a pressure switch 660 that enables/disables the pumps 600, 700. In one embodiment the pressure switch disables the booster pump 600 if the pressure exceeds a given value. The pressure switch 660 may re-enable booster pump once the pressure drops a given amount below the set pressure. Alternatively, the pressure switch 660 may disable the booster pump 600 and the recirculation pump 700 if the pressure exceeds a pre-determined value. The pressure switch 660 may re-enable the booster pump 600 and the recirculation pump 700 once the pressure drops a given amount below the set pressure.

An alternative embodiment of the cross-flow filter system 601 may include a permeate valve 644 on line 643 to control the flow of permeate through the filter membrane. The permeate valve 644 may for example be closed after the system 601 is primed to allow the feed fluid to circulate through filter 800 without permeating through the membrane. This may be useful, for example, with the microfiltration of blood. Prior to filtering operations, it may be beneficial to allow the blood to flow through the filter without permeating across the filter membrane in order to improve the hemo-compatibility of the filter components and to reduce membrane fouling. In another implementation, the permeate valve 644 may be closed to facilitate backflushing of the filter membrane as the feed flow past the membrane creates a reversed pressure gradient across the membrane.

In another embodiment, the cross-flow filter system 601 may include a third pump 646 along the permeate fluid conduit 643. The permeate pump 646 may be used to control the rate of permeate flow in conduit 643. The concentration of the retained material in the recirculation loop may also be controlled by the combined action of the pumps 646, 600 and the flow restrictor 122. Additionally, the permeate pump 646 may be a reversible flow pump, so that it may flow permeate back through the membrane into the cross-flow filter retentate stream. The permeate pump 646 may be used to backflush the filter membrane periodically. A reverse flow through the filter may dislodge particles, scale and biofilm that aggregate on the surface of the filter core. The back-flushing procedure may require a separate reservoir of permeate-compatible fluid to be used as the backflushing fluid. For example, in a bloodprocessing system, a container of plasma may be used, either vented for sterile air ingress, or constructed of a non-vented collapsible bag.

In the following discussion, reference will be made to an exemplary embodiment comprising a blood treatment system in which plasma is separated from blood using a cross-flow plasma filter, following which the plasma may then be treated by removal of particular biological materials or chemical compounds through an appropriately selected adsorption filter. It should be noted, however, that the invention is not limited to the filtering of blood and plasma, or even of other biological fluids (such as, e.g., dialysate solution). The invention may be applied to any liquid containing dissolved or suspended solutes or particles for which cross-flow filtration followed by adsorption filtration would be useful. In blood treatments systems, it should be noted that a biological fluid other than plasma may be extracted from blood depending on the type of cross-flow filter selected. The subsequent passage of this fluid through an adsorption filter, and the recirculation features of the invention will apply equally well to this type of fluid.

Figure 3:
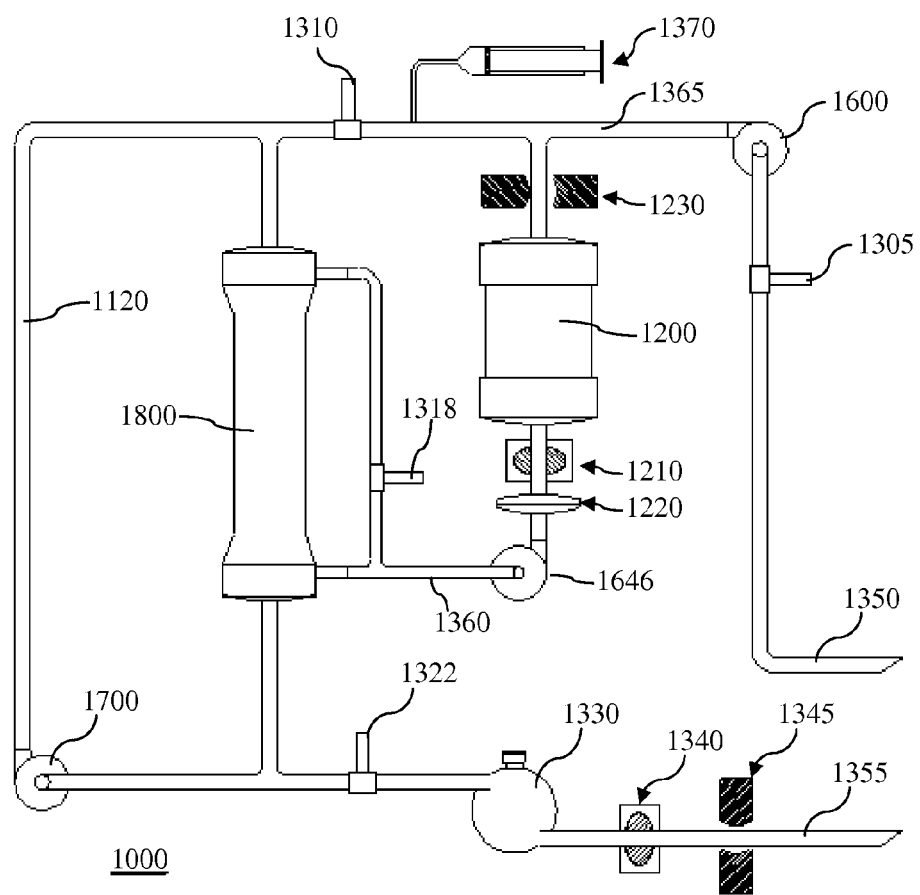
FIG. 3 is a schematic representation of a cross-flow filter linked to an adsorption filter with recirculation loop.

In one embodiment a fluid treatment module 1000 may incorporate a first return loop that returns the retentate of the membrane filter exit to the inlet of the membrane filter and incorporates a second return loop that returns the permeate to the inlet of the membrane filter as shown in FIG. 3. In applications in which plasma is separated from whole blood in the membrane filter, returning the plasma to the membrane filter intake maintains the blood hematocrit at more physiologic levels to reduce problems such as, for example, clumping, clotting or hemolysis in the membrane filter. In FIG. 3, the permeate (or, e.g., separated plasma) is further filtered by an adsorption filter 1200 to remove a particular contaminant, which may include (and is not limited to) one or more of the following: toxins, particulates, cytokines, viruses, and biological or chemical contaminants. The flow through the return loop 1120 is much higher than the flow of fluid (e.g., blood) into and out of the treatment module 1000 through the input and output lines 1350, 1355. A fraction of the fluid or plasma entering cross-flow filter 1800 is pulled across the filter media by permeate pump 1646 and then flowed through and treated by the absorption filter 1200. The treated permeate may then be returned to the incoming feed line 1365, where it mixes with the incoming fluid (such as, e.g., whole blood in an extracorporeal treatment system). This mixture of source fluid or whole blood and treated permeate or plasma then mixes with the recirculating fluid or blood mixture from line 1120 before reentering filter 1800. The ratio of flow through the return loop 1120 relative to the intake flow in 1350 and the ratio of permeate or plasma flow in the permeate line 1360 relative to the intake flow in line 1350 may be selected so that most of the permeate or plasma flows through the adsorption filter 1200 many times before exiting the fluid treatment module 1000. The multiple passages through the adsorption filter 1200 allow the fluid treatment module 1000 to reduce the concentration of contaminants to any desired level and well below what could be achieved in a single pass through the adsorption filter 1200. The fluid treatment module 1000 can be operated to produce a specified level of decontamination by selecting the appropriate ratios of recirculation and permeate flow relative to the inlet flow into the fluid treatment module and knowing the pre-determined rate of adsorption or filtering in the adsorption filter 1200 for the given contaminant.

In an extracoporreal treatment system, the fluid treatment module 1000 may be connected to a patient's blood supply via access line 1350. Processed blood is returned via line 1355.

A controller (not shown) may provide power to and/or may control the speed of the pumps 1600, 1646, 1700, and control the operation of various valves in the system. The controller may also monitor signals from one or more pressure sensors 1305, 1310, 1318, 1322. The controller may also monitor the signals from temperature sensors, conductivity sensors and/or oxygen concentration sensors. The supply pump 1600 pulls the blood into the fluid treatment module 1000 and returns it to the patient. The supply pump 1600 may be controlled to provide a specific rate of flow through the fluid treatment module 1000. Alternatively, the supply pump 1600 may be controlled to provide a desired pressure as measured by the feed pressure sensor 1310. In addition, the supply pump 1600 may be controlled to limit any negative pressure created in the access line 1350 as measured by the access pressure sensor 1305. The treated permeate or plasma from the adsorption filter 1200 may enter the feed line 1365 and mix with the fluid entering the system (e.g., whole blood) from the supply pump 1600.

In some examples, a chemical or medication (such as heparin) may be infused in the feed line 1365 from a pump 1370. The medication pump 1370 may be any assembly suitable to deliver a controllable amount of medication based on the flow rate of the source fluid (e.g., whole blood) through the supply pump 1600. The medication pump 1370 may be selected from known pump technologies including but not limited to syringe pumps, rotary peristaltic pumps, linear peristaltic pumps, pneumatically controlled diaphragm pumps. In an extracorporeal system, heparin is a well known anti-coagulant that is typically added to reduce clotting and agglomeration of blood. A chemical or medication may be added at a rate that is specified fraction of the incoming source fluid, such as whole blood. The controller (not shown) may control the flow rate of the medication pump 1370 based on a signal indicative of the source fluid flow rate. The source fluid (e.g., blood) flow rate signal may be the speed of the supply pump 1600 or may be calculated from one or both pressures measured by sensors 1305, 1310.

The mixture of treated permeate and source fluid may then mix with the recirculating fluid from return line 1120 before entering the cross-flow filter 1800. In the case of an extracorporeal blood treatment system, the mixture of treated plasma and whole blood mixes with the recirculating blood mixture from the return line 1120 before entering the plasma filter 1800. A fraction of the fluid entering filter 1800 flows across the filter medium to enter the permeate line 1360. The flow across the filter medium is controlled in part by the permeate pump 1646 which may create a pressure difference across the filter medium that drives the flow of permeate. The controller (not shown) may vary the permeate pump 1646 to achieve a desired pressure in the permeate line 1360 as measured by the permeate pressure sensor 1318. Alternatively, the permeate pump 1646 may controlled to achieve a desired pressure difference across filter 1800 as measured by the difference of the arterial and permeate pressure sensors 1310, 1318.

In extracorporeal blood treatment systems, a hemoglobin detector 1210 may be placed in the permeate line 1360 to detect failure in the plasma filter 1800. The hemoglobin detector 1210 would react to either whole blood cells or the components of red blood cells. Whole red bloods may enter the plasma line 1360 if the filter media has a tear or break allowing whole blood to enter the plasma line 1360. Red blood cell components may enter the plasma line 1360, due to hemolysis in the filter or recirculation pump. Hemolysis or red blood cell destruction may occur in the plasma filter if red blood cells plate out on the surface or are sheared apart near the surface of the filter media. The controller may monitor the signal from the hemoglobin detector. The controller may issue a warning if the signal of the hemoglobin detector exceeds a given level but is less than a second higher level. The controller may further vary the speed the return pump or the plasma pump in response to the detection of a low level of hemoglobin. The controller may issue an alarm if the hemoglobin detector signal exceeds a second pre-determined threshold. The controller may also initiate a shut-down of the treatment module 1000, when it issues an alarm due to the presence of a pre-determined level of hemoglobin in the plasma line 1360.

The Adsorption filter 1200 may be any permeate treatment device that removes contaminants from the permeate flowing through it. Adsorption filter 1200 may include (but not be limited to) a charcoal or activated carbon adsorption column. Other examples may include leptin adsorption filters such as the Aethlon Hemopurifier® made by Aethlon Medical Inc., endotoxin filters such as the PMX-20R® made by Toray Industries, Inc. and cytokine extractors such as the CytoSorb® system made by CytoSorbents, Inc. These elements may adsorb pathogens in the permeate non-selectively such as a charcoal or may be designed to selectively adsorb a particular pathogen or toxin. The adsorbed elements remain in the adsorption filter 1200, while the treated permeate exits before mixing with the incoming source fluid (such as whole blood).

The permeate line may include a variable volume chamber 1220 (which may, for example, comprise a collapsible chamber having compliant walls) to facilitate backflushing the filter 1800. The backflushing may be accomplished during operation of the treatment module 1000 by closing the backflush clamp 1230 and allowing the variable volume chamber 1220 to fill with pressurized liquid. Then the permeate pump 1646 may be driven backward to push permeate back across the filter medium. Backflushing the filter 1800 may help to dislodge particles and cellular elements that may clog the filter medium.

The fluid that flows through the filter 1800 and not across the filter medium exits the filter as the retentate. In an extracorporeal treatment system, most of this mixture of red cells and plasma is recirculated to the inlet of the plasma filter by the return pump 1700. The return pump 1700 may produce a flow rate in the return line 1120 that is higher than the inlet 1365 flow rate. In some embodiments, the return line flow rate can range up to about twice as high as the inlet flow rate. In other embodiments the return line flow rate can be higher than twice the inlet flow rate. The controller (not shown) may control the speed of the return pump 1700 to maintain a given ratio of the speed of the supply pump 1600. Alternatively, the return pump 1700 may be controlled based on the characteristics of filter 1800. In addition, the return pump 1700 may be controlled based on the desired therapy, which determines the type of filter and adsorption filter chosen, and the desired rate of contaminant removal.

A small fraction of the retentate exiting the filter 1800 will flow toward the exit of the treatment module 1000 via line 1355. In an extracorporeal blood treatment system, protamine may be infused into the exiting line 1355 to reverse any administered heparin. The exit line 1355 may include elements to protect a patient from air entering their blood stream. The first element may be an air trap 1330 to trap gases that may evolve from the blood or that may otherwise enter the fluid flow paths of the treatment system. The air trap 1330 may be, for example, a 'run-full' air trap similar to that disclosed in US Patent Application Publication no. 2009/0114582. The second element may be an Air-In-Line (AIL) detector 1340 that detects the presence of gas bubbles or foam in the blood exiting the treatment module 1000. The controller may monitor the AIL signal and issue a warning if the detected gas level exceeds a first threshold and remains less than a second threshold. If the AIL signal exceeds the second threshold, the controller may signal an alarm and stop the flow of blood by turning off at least the supply pump 1600 and closing outlet clamp 1345.

Figure 4:
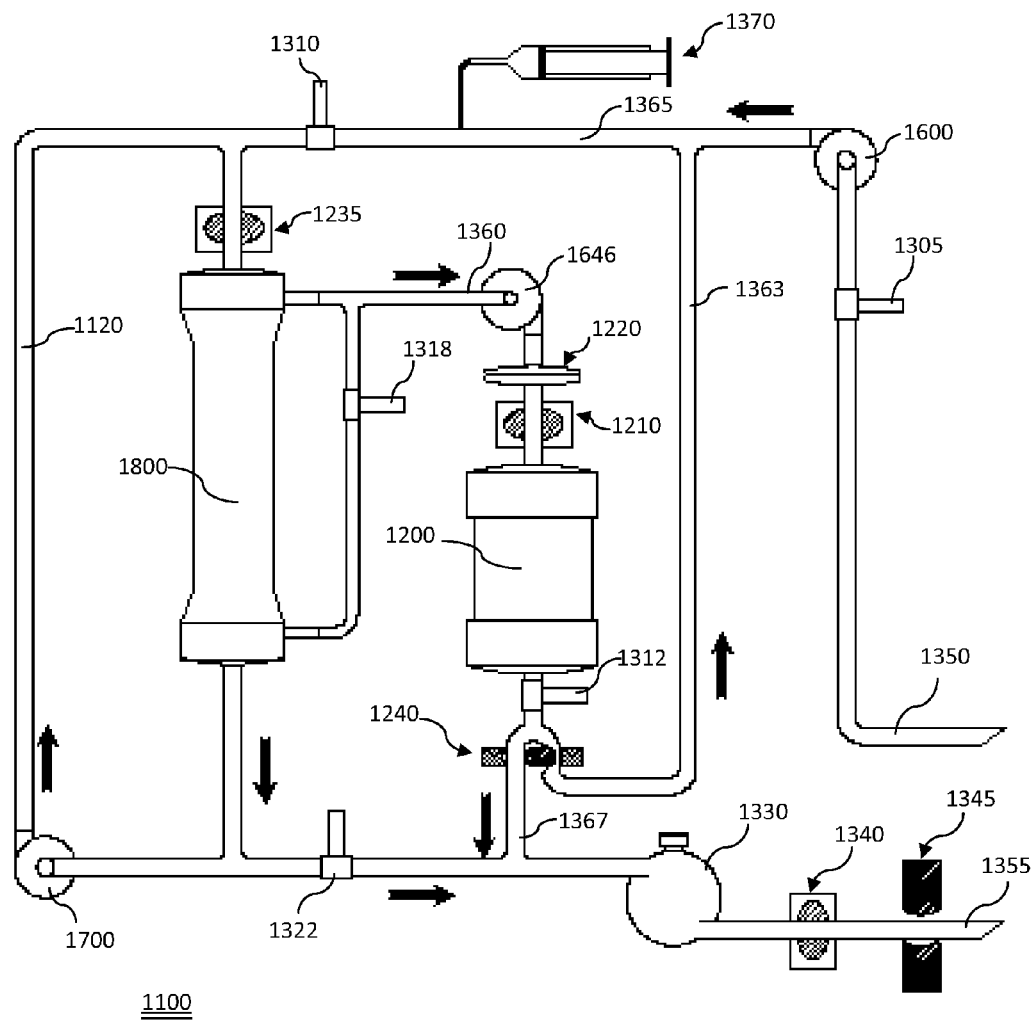
FIG. 4 is a schematic representation of an alternative embodiment of a cross-flow filter linked to an adsorption filter with recirculation loop.

Another embodiment of a Treatment Module 1100 is shown in FIG. 4 and is referred herein as the post dilution treatment module. Similar to the treatment module 1000, the post-dilution treatment module 1100 includes a supply pump 1600 to control the flow of source fluid (such as blood) into the system, a return pump 1700 to recirculate retentate from the membrane filter 1800 to the filter inlet and a permeate pump 1646 to control the flow of permeate through the filter material. Similar to the treatment module 1000, the post-dilution treatment module 1100 may recirculate the retentate so that the flow rate through the cross-flow membrane filter is high enough to reduce fouling of the filter surface. The supply pump 1600 and return pump 1700 may be controlled as described above. The use of a medication pump 1370, a sensor such as a hemoglobin sensor 1210, air trap 1330, AIL sensor 1340 and valve 1345 are the same as described in the treatment module 1000 description.

The controller (not shown) may vary the speed of the permeate pump 1646 to achieve the desired flowrate across the cross-flow filter media and provide enough pressure to deliver the flow to either the feed line 1365 or the outflow line 1355. The controller may also vary the speed of the permeate pump 1646 to achieve a desired pressure difference or limit the pressure difference across the cross-flow filter media. The speed of the permeate pump 1646 may be selected by the controller based on one or more from the following pressure sensors feed pressure sensor 1310, permeate pressure sensor 1318, and the permeate outlet pressure sensor 1312.

The post-adsorption treatment module 1100 allows the treated permeate to be directed to either the feed line 1365 or the outlet line 1355. If the adsorption filter 1200 is particularly efficient, the desired level of contamination reduction may be achieved by a single pass of permeate through it. In that case, it may be preferable to limit the number of repeated transits of treated permeate across the cross-flow filter 1800 and adsorption filter 1200. In this case the 3-way valve 1240 at the exit of the adsorption filter 1200 may be commanded by the controller (not seen) to direct the treated permeate toward the outlet line 1355.

The post-dilution treatment module 1100 may include a sensor (such as, e.g., a conductivity sensor or hematocrit sensor) 1235 upstream of the membrane filter inlet to signal the controller (not shown) if the solute concentration of the recirculating fluid, (or the hematocrit concentration in an extracorporeal treatment system) exceeds a threshold value. Excessively concentrated fluid may foul the membrane filter 1800. In an extracorporeal treatment system, an excessively high hematocrit may cause increased hemolysis or more rapid clogging of the membrane of filter 1800. The controller (not shown) may respond to excessive solute or particulate concentration levels by directing the 3-way valve 1240 to a position in which more of the treated permeate is sent to the feed line 1365 via line 1363. The returned permeate will reduce the concentration of the recirculating fluid. The 3-way valve may also be adjusted by switching between the two positions or by being held in an intermediate position that will direct some but not all of the treated permeate to the fill line 1365. Proportional control of valve 1240 may allow control the solute or particulate concentration of the recirculating fluid to a desired or pre-determined level.

The invention claimed is:

1. A blood filtration apparatus comprising:
   a source blood conduit configured to fluidly connect a source blood inlet to an inlet of a cross-flow plasma filter;
   a recirculation conduit configured to recirculate plasma-separated blood from a retentate outlet of the cross-flow plasma filter to the inlet of the cross-flow plasma filter, forming a recirculation loop;
   a first pump fluidly disposed within the recirculation loop and configured to recirculate plasma-separated blood from the retentate outlet to the inlet of the cross-flow plasma filter,
   an outlet conduit from the recirculation loop fluidly connected to a first outlet of the blood filtration apparatus;
   a plasma permeate conduit fluidly connecting a plasma permeate outlet of the cross-flow plasma filter to an adsorption filter for adsorption filtering of plasma permeate;
   an outlet of the adsorption filter connected to the recirculation loop; and
   a second pump disposed within the plasma permeate conduit configured to pump plasma permeate between the plasma permeate outlet of the cross-flow plasma filter and the adsorption filter; wherein
   the second pump is configured to pump a quantity of the plasma permeate into the recirculation loop.

2. The apparatus of claim 1, wherein the outlet of the adsorption filter is connected to the source blood conduit.

3. The apparatus of claim 1, further comprising a third pump disposed within the source blood conduit, the third pump configured to pump a source of blood into the recirculation loop.

4. The apparatus of claim 1, further comprising a flow restrictor within the outlet conduit.

5. The apparatus of claim 1, further comprising a valve disposed within the plasma permeate conduit and a variable volume chamber interposed between the valve and the second pump, wherein the variable volume chamber is configured to fill with plasma permeate upon closure of the valve.

6. The apparatus of claim 1, wherein the first pump or the second pump comprises a peristaltic pump, a centrifugal pump, an axial pump, a diaphragm pump or a reciprocating pump.

7. A filtration system comprising:
   a source fluid conduit configured to fluidly connect a source fluid inlet to an inlet of a cross-flow filter;
   a recirculation conduit configured to recirculate fluid from a retentate outlet of the cross-flow filter to the inlet of the cross-flow filter, forming a recirculation loop;
   a first pump fluidly disposed within the recirculation loop and configured to recirculate fluid from the retentate outlet to the inlet of the cross-flow filter,
   an outlet conduit from the recirculation loop fluidly connected to a first outlet of the filtration system;
   a permeate conduit fluidly connecting a permeate outlet of the cross-flow filter to an adsorption filter for adsorption of permeate;
   an outlet of the adsorption filter connected to the recirculation loop;
   a second pump disposed within the permeate conduit configured to pump permeate between the permeate outlet of the cross-flow filter and the recirculation loop;
   a third pump disposed within the source fluid conduit, the third pump configured to pump a source fluid into the recirculation loop;
   a controller configured to control the first, second and third pumps,
   wherein the controller controls the first, second or third pumps so that a predetermined fraction of the permeate is returned to the recirculation loop.

8. The filtration system of claim 7, wherein the controller is configured to control the output of the second pump or the third pump to be a predetermined fraction of the output of the first pump.

9. The filtration system of claim 7, wherein the permeate conduit comprises a first branch fluidly connected to the recirculation loop and a second branch fluidly connected to the outlet conduit, a valve being interposed at a junction of the branches to selectively restrict fluid flow in one or both of the branches.

10. The filtration system of claim 9, wherein the source fluid is blood, the cross-flow filter is a plasma filter, and a hematocrit sensor is positioned in the recirculation loop, and wherein the controller receives data from the hematocrit sensor and is configured to adjust the valve to regulate flow to the first branch based on the hematocrit data.

11. A filtration method comprising the steps:
   supplying fluid from a source to an inlet of a cross-flow filter;
   recirculating fluid from a retentate outlet of the cross-flow filter to the inlet of the cross-flow filter;
   passing a permeate fluid from a permeate outlet of the cross-flow filter through an adsorption filter;
   recirculating the permeate fluid from an outlet of the adsorption filter to the inlet of the cross-flow filter;
   returning a portion of the fluid from the retentate outlet of the cross-flow filter to the source.

12. A blood filtration system comprising:
   a source blood conduit configured to fluidly connect a source blood inlet to an inlet of a cross-flow plasma filter;
   a recirculation conduit configured to recirculate plasma-separated blood from a retentate outlet of the cross-flow plasma filter to the inlet of the cross-flow plasma filter, forming a recirculation loop;
   a first pump fluidly disposed within the recirculation loop and configured to recirculate plasma-separated blood from the retentate outlet to the inlet of the cross-flow plasma filter;
   an outlet conduit from the recirculation loop fluidly connected to a first outlet of the blood filtration system;
   a plasma permeate conduit fluidly connecting a plasma permeate outlet of the cross-flow plasma filter to an adsorption filter for adsorption filtering of plasma permeate;
   an outlet of the adsorption filter connected to the recirculation loop;
   a second pump configured to pump plasma permeate between the plasma permeate outlet of the cross-flow plasma filter and the adsorption filter, or between the adsorption filter and the recirculation loop; and
   a controller configured to control the first and second pumps,
   wherein the controller controls the first and second pumps so that a predetermined fraction of the plasma permeate is returned to the recirculation loop.

13. The blood filtration system of claim 12, wherein the controller controls the first and second pumps so that the output of the second pump is a predetermined fraction of the output of the first pump.

14. The blood filtration system of claim 12, wherein the plasma permeate conduit comprises a first branch fluidly connected to the recirculation loop and a second branch fluidly connected to the outlet conduit, and wherein the controller controls a valve at a junction of the branches to selectively restrict plasma permeate flow in one or both of the branches.

15. The blood filtration system of claim 14, further comprising a hematocrit sensor positioned in the recirculation loop, wherein the controller is configured to receive data from the hematocrit sensor and is configured to adjust the valve to regulate flow of plasma permeate to the first branch based on the hematocrit data.

16. A blood filtration method comprising the steps:
supplying blood from a source to an inlet of a cross-flow plasma filter;
recirculating plasma-separated blood from a retentate outlet of the cross-flow plasma filter to the inlet of the cross-flow plasma filter;
passing a plasma permeate from a plasma permeate outlet of the cross-flow plasma filter through an adsorption filter;
recirculating a first portion of the plasma permeate from an outlet of the adsorption filter to the inlet of the cross-flow plasma filter;
returning a second portion of the plasma permeate from the outlet of the adsorption filter and a portion of the plasma-separated blood from the retentate outlet of the cross-flow plasma filter to the source.

\* \* \* \* \*